US008916723B2

(12) United States Patent
Das et al.

(10) Patent No.: US 8,916,723 B2
(45) Date of Patent: Dec. 23, 2014

(54) SUBSTITUTED CYCLOHEXANE-1, 3-DIONE COMPOUNDS, PROCESS FOR PREPARATION THEREOF AND ITS APPLICATIONS

(75) Inventors: Pralay Das, Palampur (IN); Dharminder Sharma, Palampur (IN); Bikram Singh, Palampur (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 13/636,431

(22) PCT Filed: Mar. 18, 2011

(86) PCT No.: PCT/IN2011/000180
§ 371 (c)(1),
(2), (4) Date: Dec. 3, 2012

(87) PCT Pub. No.: WO2011/117881
PCT Pub. Date: Sep. 29, 2011

(65) Prior Publication Data
US 2013/0079545 A1 Mar. 28, 2013

(30) Foreign Application Priority Data
Mar. 22, 2010 (IN) .............................. 677/DEL/2010

(51) Int. Cl.
C07C 69/76 (2006.01)
C07C 59/205 (2006.01)
C07C 45/45 (2006.01)
C07C 67/31 (2006.01)
C07C 67/347 (2006.01)
C07C 69/716 (2006.01)
C07C 45/00 (2006.01)
C07C 51/09 (2006.01)
C07C 51/367 (2006.01)

(52) U.S. Cl.
CPC ............. *C07C 59/205* (2013.01); *C07C 45/455* (2013.01); *C07C 67/31* (2013.01); *C07C 67/347* (2013.01); *C07C 69/716* (2013.01); *C07C 45/00* (2013.01); *C07C 51/09* (2013.01); *C07C 51/367* (2013.01); C07C 2101/14 (2013.01)
USPC ......................................................... 560/55

(58) Field of Classification Search
USPC .................................................. 560/55, 126
See application file for complete search history.

(56) References Cited

U.S. PATENT DOCUMENTS 3,950,420 A 4/1976 Sawaki et al.
4,511,391 A 4/1985 Serban et al.
4,604,132 A 8/1986 Conway et al.
4,639,267 A 1/1987 Farquharson et al.
4,652,303 A 3/1987 Watson et al.
4,844,735 A 7/1989 Jahn et al.
5,162,602 A 11/1992 Somers et al.
2006/0084173 A1* 4/2006 Poole et al. ..................... 436/57

FOREIGN PATENT DOCUMENTS

EP 0496630 A1 7/1992
EP 0946101 A1 10/1999
WO 94/03443 A1 2/1994
WO 98/24321 A1 6/1998
WO 2004/093805 A2 11/2004

OTHER PUBLICATIONS

Ishikawa et al. (Revisiting [3+3] Route to 1,3-Cyclohexanedione Frameworks: Hidden Aspect of Thermodynamically Controlled Enolates, J. Org. Chem., 66, pp. 8000-8009, 2001).*
Huang et al. (Cyclization of 4-isob|Ultyrylpimelic acid and 3,3-bis(cyanoethyl)-2,4-hexanedione, Huaxue Xuebao, 44(7), 738-41, 1986).*
Walker, (Reduction of Phenols. New Synthesis of Oxyhexahydro-3 ketophenanthrenes by Cyclodehydration of 4-(β-Arylethyl)- 1,3-cyclohexandiones, Journal of the American Chemical Society, vol. 80, pp. 645-652, 1958).*
Karin Leijondahl, et al; "Efficient Ruthenium-Catalyzed Transfer Hydrogenation/Hydrogenation of 1,3-Cycloalkanediones to 1,3-Cycloalkanediols Using Microwave Heating", J. Org. Chem., vol. 71, pp. 8622-8625; Publication Date (Web): Oct. 5, 2006.
E.A. Lock, et al; "From toxicological problem to therapeutic use: The discovery of the mode of action of 2-(2-nitro-4-trifluoromethylbenzoyl)-1,3-cyclohexanedione (NTBC), its toxicology and development as a drug", J. Inherit. Metab. Dis. vol. 21, pp. 498-506; Aug. 1998.
Na Li, et al; "Bioactive Polyketides from *Peperomia duclouxii*", J. Nat. Prod. vol. 70, pp. 998-1001; Published on Web: Jun. 5, 2007.
Cara E. Humphrey, et al; "Solid-Supported Cyclohexane-1,3-dione (CHD): A "Capture and Release" Reagent for the Synthesis of Amides and Novel Scavenger Resin", Organic Letters, vol. 5, No. 6, pp. 849-852; Published on Web: Feb. 15, 2003.

(Continued)

*Primary Examiner* — Brandon Fetterolf
*Assistant Examiner* — Blaine G Doletski
(74) *Attorney, Agent, or Firm* — Ladas & Parry LLP

(57) ABSTRACT

A regio-selective and consecutive Michael-Claisen process has been developed for substituted cyclohexane-1,3-dione synthesis started from unsubstituted or substituted acetone and α,β-unsaturated esters. Substituted cyclohexane-1,3-diones are the basic unit found in several natural products, bioactive alkaloids and acridine dione type heterocycles, polyphenols, and unnatural amino acid synthesis. Most of the potent herbicidal and pesticidal active molecules contain cyclohexane-1,3-dione derivatives. Such an important intermediate synthesis using a facile, atom economy and one-pot process is a demandable area in organic synthesis.

12 Claims, No Drawings

(56) References Cited

OTHER PUBLICATIONS

Basudeb Basu, et al; "KF-Alumina-Mediated Selective Double Michael Additions of Aryl Methyl Ketones: A Facile Entry to the Synthesis of Functionalized Pimelate Esters and Derivatives", Synlett, No. 12, pp. 2224-2226; Advanced online publication: Mar. 9, 2004.

Teruhiko Ishikawa, et al; "Revisiting [3+3] Route to 1,3-Cyclohexanedione Frameworks: Hidden Aspect of Thermodynamically Controlled Enolates", The Journal of Organic Chemistry, vol. 66, No. 24, pp. 8000-8009; Nov. 30, 2001.

Teruhiko Ishikawa, et al; "Domino Double Michael-Claisen Cyclizations: A Powerful General Tool for Introducing Quaternary Stereocenters at C(4) of Cyclohexane-1,3-diones and Total Synthesis of Diverse Families of Sterically Congested Alkaloids", J. Org. Chem., vol. 73, pp. 7498-7508; Published on Web: Sep. 10, 2008.

Philip Alferness, et al; "Determination of Mesotrione Residues and Metabolites in Crops, Soil, and Water by Liquid Chromatography with Fluorescence Detection", Journal of Agricultural and Food Chemistry, vol. 50, pp. 3926-3934, Published on Web Jun. 1, 2002.

Glynn Mitchell, et al; "Mesotrione: a new selective herbicide for use in maize", Pest Management Science, vol. 57, pp. 120-128; Feb. 2001.

Tae-Joon Kim, et al; "EK-2612, a new cyclohexane-1,3-dione possessing selectivity between rice (*Oryza sativa*) and barnyardgrass (*Echinochloa crus-galli*)", Pest Management Science, vol. 60, pp. 909-913; Published online May 13, 2004.

John N. Gardner, et al; "The Total Synthesis of Some (±)-18-Methyl-9β, 10α-androstanes and (±)-18-Methyl-9β, 10α-D-homoandrostanes", J. Org. Chem. vol. 34, No. 1, pp. 107-112; Jan. 1969.

Ulrich Eder, et al; "New Type of Asymmetric Cyclization to Optically Active Steriod CD Partial Structures", Angew. Chem. Internal. Edit. vol. 10, No. 7, pp. 496-497; Jul. 1, 1971.

George R. Newkome, et al; "Synthesis, Resolution, and Stereochemistry of 5-Hydroxy-10-alkyl-$\Delta^{1(9)}$-2-octalones", J. Org. Chem. vol. 37, No. 13, pp. 2098-2101, : Publication Date: Jun. 1972.

Zoltan G. Hajos, et al; "The Stereocontrolled Synthesis of *trans*-Hydrindan Steroidal Intermediates", J. Org. Chem., vol. 38, No. 19, pp. 3239; Sep. 21, 1973.

Jeong Mi Kim, et al; "Oxidative Aromatization of 2-Acylcyclohexane-1,3-dione Derivatives Using Iodine in Methanol", Bull. Korean Chem. Soc., vol. 24, No. 8, pp. 1057-1058: Journal Year 2003.

T.R. Kasturi, et al; "Acylation and alkylation of 1,3-dimethoxybenzene in polyphosphoric acid", Canadian Journal of Chemistry, vol. 47, No. 9, pp. 1529-1535, May 1969.

Huamin Huang, et al; "Cyclization of 4-isobutyrylpimelic acid and 3,3-bis(cyanoethyl)-2,4-hexanedione", Database Caplus [Online] Chemical Abstracts Service, Columbus, Ohio, U.S. 1987; XP002649656; Database accession No. 1987:119615 abstract, Considered to the extent of pictures and abstract.

International Search Report: mailed Sep. 20, 2011; PCT/IN2011/000180.

\* cited by examiner

SUBSTITUTED CYCLOHEXANE-1, 3-DIONE COMPOUNDS, PROCESS FOR PREPARATION THEREOF AND ITS APPLICATIONS

FIELD OF THE INVENTION

The present invention relates to substituted cyclohexane-1,3-dione compounds of general formula I

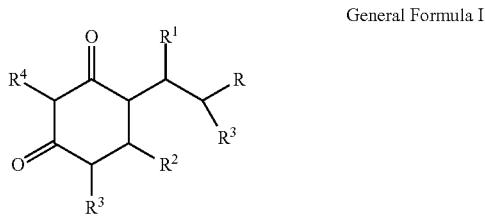

General Formula I wherein,
R is selected from $CO_2Y$, $B(OY)_2$, CHO, $CH_2OY$, $CH(CO_2Y)_2$, $PO(OY)_2$ and CONHZ, wherein Y is selected from the group consisting of hydrogen, alkyl, alkenyl, alkynyl, aryl, heteroaryl, substituted alkyl, substituted alkenyl, cycloalkyl, substituted alkyl, substituted heteroaryl or tetrazolyl and Z is selected from the group consisting of hydrogen, hydroxyl, alkyl, alkyl-sulfonyl, unsubstituted or substituted aryl sulfonyl, cynoalkyl and COXM wherein X is selected from S, SO or $SO_2$ and M is selected from hydrogen, alkyl, unsubstituted or substituted alkyl, unsubstituted or substituted aryl, unsubstituted or substituted heteroaryl;
$R^1$ and $R^2$ is selected from the group consisting of hydrogen, alkyl, unsubstituted aryl, substituted aryl, unsubstituted heteroaryl, substituted heteroaryl, substituted alkyl, unsubstituted cycloalkyls or substituted cycloalkyls;
$R^3$ is selected from the group consisting of hydrogen, alkyl, alkoxy, substituted or unsubstituted aryl, substituted or unsubstituted heteroaryl;
$R^4$ is selected from the group consisting of hydrogen, alkyl, heteroalkyl, unsubstituted or substituted alkyl, substituted or unsubstituted aryl, unsubstituted or substituted heteroaryl, alkoxy, substituted or unsubstituted aryl carbonyl or substituted keto compounds.

The present invention particularly relates to a process for preparation of substituted cyclohexane-1,3-dione compounds of general formula I from alkyl carbonyls.

The present invention further relates to substituted cyclohexane-1,3-dione compounds of general formula I useful as an intermediate for the synthesis of several biological active heterocycles, natural product analogues, anisoles and aromatic poly phenol derivatives.

The present invention further relates to a convenient, inexpensive, and efficient method for the synthesis of substituted cyclohexane-1,3-dione compounds of general formula I.

BACKGROUND OF THE INVENTION

Cyclohexanone-1,3-diones play an important role in organic synthesis due to their usefulness in the preparation of many biological important compounds. Cyclohexane-1,3-diones refer to an important class of compounds known for their herbicidal activity and anti-inflammatory activity. Cyclohexane-1,3-diols are useful building blocks in pharmaceuticals and can be easily prepared from cyclohexane-1,3-dione derivatives (Leijondahal, K.; Fransson, A. L.; Backvall, J. *J. Org. Chem.* 2006, 71, 8622-8625). 2-(substituted)-1,3-cyclohexanedione (Cain, P. A.; Cramp, S. M. European Patent E0496630) such as NTBC is a triketone with herbicidal activity i.e. potent inhibitor of enzyme 4-hydroxyphenyl pyruvate dioxygenase (HPPD) in plants and developed as drug to cure children with a rare inborn error of metabolism (Lock, E; A.; Ellis, M. K.; Gaskin, P.; Robinson, M.; Auton, T. R.; Provan, W. M.; Smith, L. L; Prisbylla, M. P.; Mutter, L. C.; Lee, D. L. *J. Inher. Metab. Dis.* 1998, 21, 498-506).

The known polyketides, surinone A and oleiferinone, showed growth inhibitory activity against the WI-138, VA-13, and HepG2 cell lines with $IC_{50}$ values that ranged from 4.4 to 9.6 micro g/ml (Li, N.; Wu, j.; Hasegawa, T.; Sakai, J.; Bai, L.; Wang, L.; Kakuta, S.; Furuya, Y.; Ogura, H.; Kataoka, T.; Tomida, A.; Tsuruo, T.; Ando, M. *J. Nat. Prod.* 2007, 70, 998-1001). Humphrey et al. used cyclohexane-1,3-dione (CHD) resin as a solid support for synthesis of amides (Humphrey, C. E.; Easson, M. A. M.; Tierney, J. P.; Turner. N. *J. Org. Lett.* 2002, 5, 849-852).

Although several methods have been reported for the synthesis of cyclohexane-1,3-dione derivatives (Ryu, E. K.; Kim, K. M.; Kim, H. R.; Song, J. H.; Kim, J. N.; Kim, J. S. WO/1994/003443) but these methods are lengthy, laborious, time consuming and costly. Few reactions have been published, where acetone under KF-Alumina basic condition gives double Michael product (Basu, B.; Das, P.; Hossain, I. *Synlett* 2004, 12, 2224-2226) and acetone derivatives under t-BuOK condition gives cyclized products with quaternary carbon at C-4 position (Ishikawa, T.; Kadoya, R.; Arai, M.; Takahash, H.; Kaisi, Y.; Mizuta, T.; Yoshikai, K.; Satio, S. *J. Org. Chem.* 2001, 66, 8000-8009).

Few studies have been reported for the synthesis of cyclohexane-1,3-dione derivatives using acetone derivatives. Reactions of substituted acetone derivatives in the presence of t-BuOK (200 mol %) in t-BuOH-THF condition performed double Michael and Claisen reaction to produce 4,4-disubstituted cyclohexane-1,3-diones (Ishikawa, T.; Kudo, K.; Kuroyabu, K.; Uchida, S.; Kudoh, T.; Saito, S. *J. Org. Chem.* 2008, 73, 7498-7508). Cyclohexane-1,3-dione derivatives and their herbicidal activities were already known in the art. For example, Alloxidim-sodium (Sawaki, M.; Iwataki, I.; Hirono, Y.; Ishikawa, H. U.S. Pat. No. 3,950,420) and Sethoxidim (Somers, D. A.; Parker, W. B.; Wyse, D. L. Gronwald, J. W.; Gengenbach, B. G. U.S. Pat. No. 5,162,602, Johnson, M. D.; Dunne, C. L.; Kidder, D. W.; Hudetz, M. EP19970953744) have come into the market as grass herbicides. Cyclohexane-1,3-dione derivatives having phenyl substituent (Serban, A.; Watson, K. G.; Bird, G. J.; Farquharson, G. J. U.S. Pat. No. 4,511,391, Farquharson; G. J.; Watson; K. G.; Bird; G. J. U.S. Pat. No. 4,639,267 and Watson, K. G.; Bird, G. J.; Farquharson, G. J. U.S. Pat. No. 4,652,303) which have structural similarities to our invention. 5-(hetero-substituted) cyclohexane-1,3-dione derivatives have herbicidal as well as plant growth regulating properties (Conway, R. J.; Watson, K. G.; Farquharson, G. J. U.S. Pat. No. 4,604,132). 5-substituted cyclohexane-1,3-dione derivatives act as herbicide for the selective control of undesirable grasses in broad-leaved crops (Jahn, D.; Rohr, W.; Becker, R.; Wuerzer, B).

References may be made to U.S. Pat. No. 4,844,735, wherein Mesotione i.e. 2-(4-methylsulfonyl-2-nitrobenzoyl)-1,3-cyclohexanedione is a new selective, pre and post emergent herbicide for control of broad-leaved and some grass weeds in corn is reported. This compound acts by competitive inhibition of the enzyme 4-hydroxy phenyl pyruvate dioxygenase (HPPD) which affects carotenoid biosynthesis ((a) Alferness, P.; Wiebe, L. *J. Agric. Food Chem.* 2002, 50, 3926-3934; (b) Mitchell, G.; Bartlett, D. W.; Fraser, T. E.;

Hawkes, T. R.; Holt, D. C.; Townson, J. K.; Wichert, R. A. *Pest. Manage. Sci.* 2001, 57, 120-128).

A new Cyclohexane-1,3-dione derivative, EK-2612 shows grass killer herbicidal activity specially in monocotyledons plants like rice and barnyard grass (Kim, T. J.; Kim, J. S.; Hong, K. S.; Hwang, I. T.; Kim, K. M.; Kim, H. R.; Cho, K. Y. *Pest. Manage. Sci.* 2004, 60, 909-913).

4-Hydroxy-2-substituted-Cyclohexane-1,3-dione i.e. polyketides are responsible for cytotoxic and anti-inflammatory bioactivities (Li, N.; Wu, J. L.; Hasegawa, T.; Sakai, J. I.; Bai, L. M.; Wang, L. Y.; Kakuta, S.; Furuya, Y.; Ogura, H.; Kataoka, T.; Tomida, A.; Tsuruo, T.; Ando, M. *J. Nat. Prod.* 2007, 70, 998-1001).

2-substituted-Cyclohexane-1,3-diones are attractive intermediates in the synthesis of natural products and in medicinal chemistry as well as pharmaceutical chemistry. They are also excellent starting materials in the natural product synthesis ((a) Gardner, J. N.; Anderson, B. A.; Oliveto, E. P. *J. Org. Chem.* 1969, 34, 107-111. (b) Eder, U.; Sauer, G.; Wiechert, R. *Angew. Chem., Int. Ed.* 1971, 10, 496-497. (c) Newkome, G. R.; Roach, L. C.; Montelaro, R. C. *J. Org. Chem.* 1972, 37, 2098-2101. (d) Hajos, Z. G.; Parrish, D. R. *J. Org. Chem.* 1973, 38, 3239-3243).

Wieland-Miescher (W-M) ketone analogue are very good intermediates for the synthesis of steroids. W-M ketone analogue is very substantial intermediate for the synthesis of pharmaceutically acceptable salts or hydrates of spiro-heterocycles, which are disclosed as selective glucocorticoid receptor modulators for treating a variety of autoimmune and inflammatory diseases or conditions (Ali, A.; Balkovec, J. M.; Beresis, R.; Colletti, S. L.; Graham, D. W.; Patel, G. F.; Smith, C. WO/2004/093805).

Cyclohexane-1,3-dione derivatives are main building block for substituted aromatic compounds synthesis. Aromatization of cyclohexane-1,3-dione derivatives have been performed using several conditions but most successful results have been observed under iodine in methanol (Kim, J. M.; Lee, K. Y.; Kim, J. N. *Bull. Korean Chem. Soc.* 2003, 24 (8), 1057-1058). To the best of our knowledge, we have developed a novel protocol for the synthesis of cyclohexane-1,3-diones not related with any methods described in above examples. Further functionalization strategies have been applied for the synthesis of several other molecules having novel structural moiety such as enaminone derivatives of cyclohexane-1,3-dione.

By using acetone, Aldol reaction was widely modified. But not a single report has been published in literature for the synthesis of such a versatile intermediate cyclohexane-1,3-dione derivatives useful in several value added organic molecules synthesis.

In summary, first time we have developed a new protocol for the synthesis of 3-(2,4-cyclohexanone)-propyl carboxylic acid ethyl ester 3 starting from acetone and ethyl acrylate in one-pot reaction. Compound 3 works as a versatile intermediate in several bioactive, value added organic molecules and natural products analogue synthesis.

OBJECTIVES OF THE INVENTION

The main objective of the present invention is to provide substituted cyclohexane-1,3-dione compounds of general formula I.

Another objective of the present invention is to provide a single pot process for preparation of substituted cyclohexane-1,3-dione compounds of general formula I which obviates the drawbacks as detailed above.

Yet another objective of the present invention is to provide 3-(2,4-cyclohexanone)-propyl carboxylic acid ester (CHPC) of formula 3 useful for the synthesis of polyphenolic bioactive compounds.

Yet another objective of the present invention is to provide substituted cyclohexane-1,3-dione compounds of general formula I useful for the synthesis of aromatic anisole derivative of propyl ester a very useful intermediate for several biological active molecules synthesis either in synthetic or biosynthetic path way.

SUMMARY OF THE INVENTION

Accordingly, present invention provides a compound of general formula I

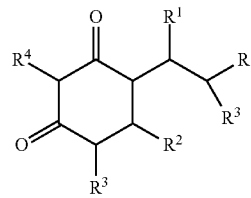

General Formula I wherein R is selected from $CO_2Y$, $B(OY)_2$, CHO, $CH_2OY$, $CH(CO_2Y)_2$, $PO(OY)_2$ and CONHZ, wherein Y is selected from the group consisting of hydrogen, alkyl, alkenyl, alkynyl, aryl, heteroaryl, substituted alkyl, substituted alkenyl, cycloalkyl, substituted alkyl, substituted heteroaryl or tetrazolyl and Z is selected from the group consisting of hydrogen, hydroxyl, alkyl, alkyl-sulfonyl, unsubstituted or substituted aryl sulfonyl, cynoalkyl and COXM wherein X is selected from S, SO or $SO_2$ and M is selected from hydrogen, alkyl, unsubstituted or substituted alkyl, unsubstituted or substituted aryl, unsubstituted or substituted heteroaryl;

$R^1$ and $R^2$ is selected from the group consisting of hydrogen, alkyl, unsubstituted aryl, substituted aryl, unsubstituted heteroaryl, substituted heteroaryl, substituted alkyl, unsubstituted cycloalkyls or substituted cycloalkyls;

$R^3$ is selected from the group consisting of hydrogen, alkyl, alkoxy, substituted or unsubstituted aryl, substituted or unsubstituted heteroaryl;

$R^4$ is selected from the group consisting of hydrogen, alkyl, heteroalkyl, unsubstituted or substituted alkyl, substituted or unsubstituted aryl, unsubstituted or substituted heteroaryl, alkoxy, substituted or unsubstituted aryl carbonyl or substituted keto compounds.

In an embodiment of the present invention, the representative compounds of general formula 1 comprising:

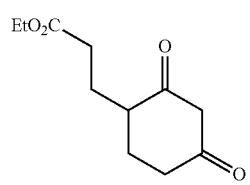

3-(2,4-cyclohexanone)-propyl carboxylic acid ethyl ester (CHPC) (Compound 3)

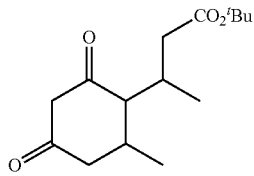

Tert-butyl 3-(2-methyl-4,6-dioxocyclohexyl) butanoate (Compound 5)

In another embodiment of the present invention, a single pot process for preparation of compound of general formula I comprising the steps of:
 i. mixing ketone compound of general formula A wherein R is selected from a group consisting of hydrogen or $(CH_2)_nX$ wherein n is a natural number being 1, 2, 3, 4, 5, 6 or 7 and X comprises hydrogen, unsubstituted or substituted alkyl

General formula A with sodium hydride (NaH) base optionally in presence of a solvent or neat at a temperature in the range of −10° C. to 0° C. to obtain a mixture;
 ii. adding α,β-unsaturated ester compound of general formula B wherein R is selected form a group consisting of H, $(CH_2)_nX$ wherein n is a natural number being 1, 2 or 3 and X comprises hydrogen, unsubstituted or substituted alkyl, unsubstituted or substituted aryl, $R^1$ is selected from the group consisting of unsubstituted and substituted alkyl group and $R^2$ is selected from the group consisting of hydrogen, unsubstituted or substituted alkyl, unsubstituted or substituted aryl

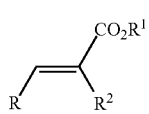

General formula B in to the mixture as obtained in step (i) at a temperature in the range of −10° C. to 0° C. and allowed to attain at 20-30° C. for a period ranging between 5 minutes to 2 h to obtain mixture;
 iii. acidifying the reaction mixture as obtained in step (ii) with HCl maintaining pH in the range of 0 to 3 followed by extracting with ethyl acetate, dichloromethane or chloroform;
 iv. concentrating the solvent the acidified mixture as obtained in step (iii) to obtain concentrate compound;
 v. purifying the concentrate compound as obtained in step (iv) by silica gel column chromatography (hexane:ethylacetate, 7:3) or by solvent extraction to obtain compound of general formula I, compound 7 and 9.

In yet another embodiment of the present invention, said process is useful for the preparation of compound of general formula II wherein $R^6$ is selected from the group consisting of hydrogen, alkyl, alkoxy, unsubstituted or substituted aryl, unsubstituted or substituted heteroaryl.

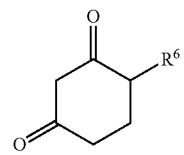

General formula II

In yet another embodiment of the present invention, representative compounds of general formula comprising:

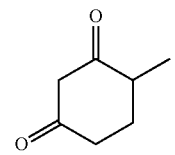

Compound 7

4-methylcyclohexane-1,3-dione

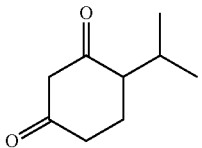

Compound 9

4-isopropylcyclohexane-1,3-dione

In another embodiment of the present invention, solvent used is selected from the group consisting of toluene, tetrahydrofuran (THF) or benzene.

In yet another embodiment of the present invention, molar concentration of sodium hydride (NaH) base is 1.5 to 2 times the number of moles of the ketone.

In yet another embodiment of the present invention, molar concentration of α,β-unsaturated ester is 1 to 2 times the number of moles of the ketone or substituted ketone.

In yet another embodiment of the present invention, solvent used for solvent extraction are selected from the group consisting of hexane, ethyl acetate, dichloromethane or chloroform.

In yet another embodiment of the present invention, said compounds are useful as an intermediate for the synthesis of several biological active heterocycles, natural product analogues, anisoles and aromatic poly phenol derivatives.

In yet another embodiment of the present invention, process for the preparation of compound of general formula III wherein $R^7$ and $R^8$ are selected from the group consisting of hydrogen, alkyl, unsubstituted or substituted alkyl and whole group $OR^7$ and $OR^8$ are selected from the group consisting of hydrogen, alkyl, substituted or unsubstituted alkyl, unsubstituted or substituted aryl using compound of general formula I

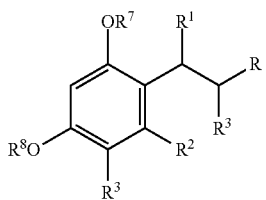

General formula III and the said process comprising the steps of; (i) reacting compound of general formula I with iodine in methanol or ethanol under reflux for a period ranging between 10 to 20 hr, (ii) diluting the reaction mixture with ethyl acetate or dichloromethane and washed with $NaHSO_3$ and brine solution, purifying the desired compound by silica gel chromatography (hexane:EtOAc, 95:5) to obtain compound of general formula III.

In yet another embodiment of the present invention, representative compound of general formula III as prepared comprising of:

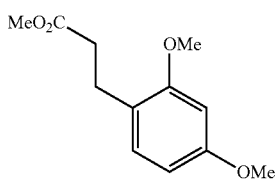

(Formula 10)

Methyl-3-(2,4-dimethoxyphenyl)propanoate

Methyl-3-(2,4-dimethoxyphenyl)propanoate
(Formula 10)

DETAILED DESCRIPTION OF THE INVENTION

Present invention provides Substituted cyclohexane-1,3-dione compounds, process for preparation thereof and its applications" which comprises double Michael and Claisen type reaction of acetone and substituted acetone with ethyl acrylate and substituted ethyl acrylate under sodium hydride basic condition in toluene solvent and neat condition at −10° C. to 0° C. of the general formula 3.

Present invention provides a method for the synthesis of 3-(2,4-cyclohexanone)-propyl carboxylic acid ethyl ester (CHPC) starting from acetone in a one-pot reaction. Accordingly, the method involves using a strong base sodium hydride (NaH), ethyl acrylate in toluene solvent. In a second aspect, the present invention is also applied for the synthesis of other cyclohexane-1,3-dione derivatives such as 5, 7 and 9. In a third aspect, the present invention is also applied for the manufacture of methyl-3-(2,4-dimethoxyphenyl)propanoate (10) synthesis which is the main building blocks of several biological active molecules.

Compound cyclohexane-1,3-dione of formula 3 is capable of providing herbicidal active cyclohexane-1,3-dione derivative type of molecules. Compound cyclohexane-1,3-dione derivative of formula 3 is a versatile intermediate for the synthesis of methyl-3-(2,4-dimethoxyphenyl) propanoate. Compound cyclohexane-1,3-dione derivative of formula 3 is capable of undergoing conversion into value added organic molecules.

Present invention provides substituted cyclohexane-1,3-dione compounds of general formula I, general formula II and general formula III

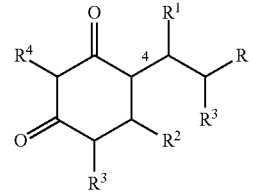

General formula I

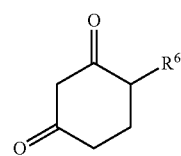

General formula II

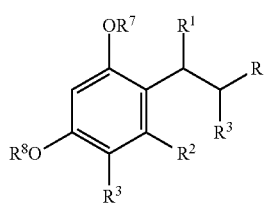

General formula III wherein R is selected from $CO_2Y$, $B(OY)_2$, CHO, $CH_2OY$, $CH(CO_2Y)_2$, $PO(OY)_2$ and CONHZ, wherein Y is selected from the group consisting of hydrogen, alkyl, alkenyl, alkynyl, aryl, heteroaryl, substituted alkyl, substituted alkenyl, cycloalkyl, substituted alkyl, substituted heteroaryl or tetrazolyl and Z is selected from the group consisting of hydrogen, hydroxyl, alkyl, alkyl-sulfonyl, unsubstituted or substituted aryl sulfonyl, cynoalkyl and COXM wherein X is selected from S, SO or $SO_2$ and M is selected from hydrogen, alkyl, unsubstituted or substituted alkyl, unsubstituted or substituted aryl, unsubstituted or substituted heteroaryl;

$R^1$ and $R^2$ is selected from the group consisting of hydrogen, alkyl, unsubstituted aryl, substituted aryl, unsubstituted heteroaryl, substituted heteroaryl, substituted alkyl, unsubstituted cycloalkyls or substituted cycloalkyls;

$R^3$ is selected from the group consisting of hydrogen, alkyl, alkoxy, substituted or unsubstituted aryl, substituted or unsubstituted heteroaryl;

$R^4$ is selected from the group consisting of hydrogen, alkyl, heteroalkyl, unsubstituted or substituted alkyl, substituted or unsubstituted aryl, unsubstituted or substituted heteroaryl, alkoxy, substituted or unsubstituted aryl carbonyl or substituted keto compounds.

$R^6$ is selected from the group consisting of hydrogen, alkyl, alkoxy, unsubstituted or substituted aryl, unsubstituted or substituted heteroaryl;

$R^7$ and $R^8$ are selected from the group consisting of hydrogen, alkyl, unsubstituted or substituted alkyl;

Whole group $OR^7$ and $OR^8$ are selected from the group consisting of hydrogen, alkyl, substituted or unsubstituted alkyl, unsubstituted or substituted aryl.

EXAMPLES

The following examples are given by way of illustration and therefore should not construed to limit the scope of the present invention.

Experimental Part

All reactions were carried out under an inert atmosphere with dry solvents under anhydrous conditions, unless otherwise stated. Toluene was freshly distilled before use and dried over 4° A molecular sieves. NaH (60%) was washed with hexane and dried under reduced pressure. Commercial reagents and solvents were of analytical grade and were purified by standard procedures prior to use. TLC was performed on Silica Gel 60 $F_{254}$ (Merck) using UV light detection. Column chromatographic separations have been carried out on normal silica gel 60-120 mesh (Merck). The $^1H$ and $^{13}C$ NMR spectra were recorded at 298 K with a Bruker AM-300 spectrometer; using TMS as internal reference standard in $CDCl_3$. HRMS spectra were determined using a Micromass Q-TOF Ultima spectrometer.

Example 1

Synthesis of 3-(2,4-cyclohexanone)-propyl carboxylic acid ethyl ester (CHPC) (formula 3)

A mixture of acetone (4 g, 68.87 mmol) and NaH (3.3 g, 137.74 mmol) was treated with ethyl acrylate (13.78 g, 137.74 mmol) in dry toluene (60 ml) at –5° C. The solution was allowed to attain room temperature (20 to 30° C.) under stirring for 2 h. The reaction mixture was acidified with 1(N) hydrochloric acid, extracted with ethyl acetate (3×15 ml) and washed with brine. The combined organic layers was dried over anhydrous $Na_2SO_4$ and concentrated under reduced pressure using rotary evaporator to evaporate the solvent. The crude product was purified by silica gel column chromatography (hexane:EtOAc, 70:30), afforded 3 as a light yellow gummy liquid (6.57 g, 45% yield).

$^1H$ NMR (300 MHz, $CDCl_3$) δ 1.21 (t, J=7.1 Hz, 6H), 1.68-1.75 (m, 4H), 2.00-2.09 (m, 4H), 2.28-2.58 (m, 10H), 3.38-3.47 (m, 2H), 4.04-4.12 (m, 4H), 5.40 (s, 1H), 6.67 (br, 1H); $^{13}C$ NMR (75 MHz, $CDCl_3$) δ 14.07, 24.26, 24.56, 25.41, 26.19, 29.76, 31.43, 31.94, 39.64, 41.27, 48.25, 58.26, 60.50, 104.01, 173.23, 173.67, 187.73, 195.15, 203.79, 204.06; HREIMS data: m/z calcd. for [M+H]$^+$ $C_{11}H_{16}O_4$ 213.2503 obsd. 213.2502.

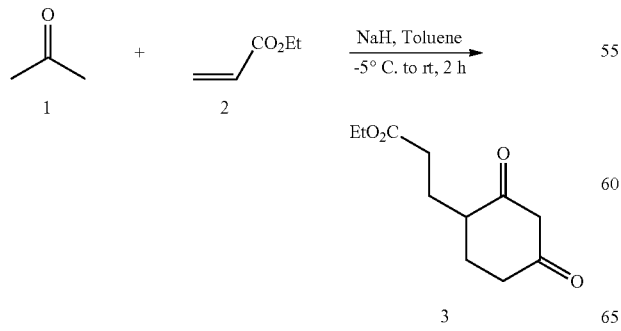

Example 2

Synthesis of 3-(2,4-cyclohexanone)-propyl carboxylic acid ethyl ester (CHPC) (formula 3) in neat condition A mixture of acetone (500 mg, 8.61 mmol) and NaH (619 mg, 15.49 mmol) was treated with ethyl acrylate (1723 mg, 17.21 mmol) at –10° C. for 5 minutes. The completion of reaction was monitor by TLC. The reaction mixture was acidified with 1(N) hydrochloric acid, extracted with ethyl acetate (3×5 ml) and washed with brine. The combined organic layers was dried over anhydrous $Na_2SO_4$ and concentrated under reduced pressure. The crude product was purified by silica gel column chromatography (hexane:EtOAc, 70:30), afforded 3 as a light yellow gummy liquid (914 mg, 50% yield).

Example 3

Synthesis of tert-butyl 3-(2-methyl-4,6-dioxocyclohexyl) butanoate (formula 5)

A mixture of acetone (500 mg, 8.60 mmol) and NaH (148 mg, 6.19 mmol) was treated with tert-butyl but-2-enoate (2448 mg, 17.21 mmol) at 0° C. in 5 ml dry toluene. The solution was allowed to attain room temperature under stirring for 2 h. The reaction mixture was acidified with 1(N) hydrochloric acid, extracted with ethyl acetate (3×5 ml) and washed with brine. The combined organic layers was dried over anhydrous $Na_2SO_4$ and concentrated under reduced pressure. The crude product was purified by silica gel column chromatography (hexane:EtOAc, 70:30), afforded 5 as light yellow semi-solid (1016 mg, 44%). $^1H$ NMR (300 MHz, $CDCl_3$) δ 1.05-1.09 (m, 6H), 1.37 (t, J=1.8, 9H), 1.51-1.56 (m, 1H), 1.79-1.86 (m, 1H), 2.06-2.21 (m, 2H), 2.42-2.49 (m, 1H), 2.56-2.64 (m, 2H), 3.24-3.48 (m, 2H), 3.24-3.31 (m, 1H), 3.42-3.48 (m, 1H); $^{13}C$ NMR (75 MHz, $CDCl_3$) δ13.50, 13.61, 17.55, 17.68, 27.72, 32.17, 32.57, 33.09, 34.03, 37.26, 38.28, 44.38, 47.44, 47.97, 58.02, 58.27, 79.96, 175.13, 175.56, 203.28, 203.87, 203.97; HREIMS data: m/z calcd. for [M+H]$^+$ $C_{15}H_{25}O_4$ 269.3566, obsd. 269.3559.

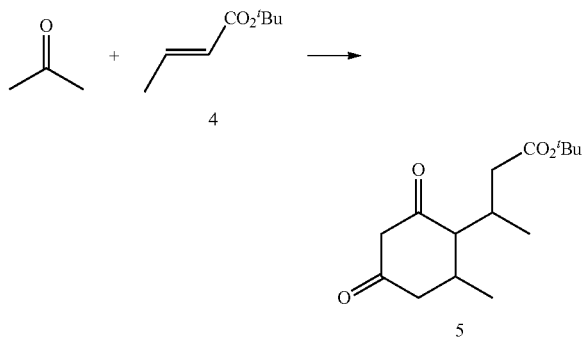

Example 4

Synthesis of 4-methylcyclohexane-1,3-dione (formula 7)

A mixture of ethyl methyl ketone (500 mg, 6.93 mmol) and NaH (415 mg, 10.39 mmol) was treated with ethyl acrylate (693 mg, 6.93 mmol) at 0° C. in 5 ml dry toluene. The solution, was allowed to attain room temperature under stirring for 2 h. The reaction mixture was acidified with 1(N) hydrochloric acid, extracted with ethyl acetate (3×5 ml) and washed with brine. The combined organic layers was dried over anhydrous $Na_2SO_4$ and concentrated under reduced pressure. The crude product was purified by silica gel column chromatography (hexane:EtOAc, 70:30), afforded 7 as a light yellow semisolid (480 mg, 55%). $^1$H NMR (300 MHz, $CDCl_3$) δ 1.22-1.28 (m, 6H), 1.48-1.77 (m, 2H), 2.02-2.20 (m, 2H), 2.36-2.71 (m, 6H), 3.35-3.49 (m, 2H), 5.4 (s, 1H), 8.40 (br, 1H); $^{13}$C NMR (75 MHz, $CDCl_3$) δ 14.20, 15.87, 26.65, 29.25, 30.20, 36.84, 39.82, 44.03, 57.89, 103.62, 188.95, 197.06, 204.20, 205.11; HREIMS data: m/z calcd. for $[M+H]^+$ $C_7H_{11}O_2$ 127.1610, obsd 127.1602.

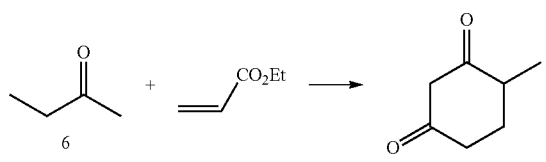

Example 5

Synthesis of 4-isopropylcyclohexane-1,3-dione (formula 9)

A mixture of 4-methylpentan-2-one (500 mg, 5 mmol) and NaH (299 mg, 7.49. mmol) was treated with ethyl acrylate (500 mg, 5 mmol) at 0° C. in 5 ml dry toluene. The solution was allowed to attain room temperature under stirring for 2 h. The reaction mixture was acidified with 1(N) hydrochloric acid, extracted with ethyl acetate (3×5 ml) and washed with brine. The combined organic layers was dried over anhydrous $Na_2SO_4$ and concentrated under reduced pressure. The crude product was purified by silica gel column chromatography (hexane:EtOAc, 70:30), afforded 9 as light yellow semisolid (400 mg, 52% yield). $^1$H NMR (300 MHz, $CDCl_3$) δ 0.86-1.25 (m, 12H), 1.71-2.09 (m, 4H), 2.14-2.74 (m, 8H), 3.33-3.53 (m, 2H), 5.48 (s, 1H), 8.19 (br, 1H); $^{13}$C NMR (75 MHz, $CDCl_3$) δ 18.61, 19.98, 20.68, 21.58, 26.92, 29.61, 30.39, 39.13, 48.10, 55.43, 58.20, 104.75, 188.19, 196.14, 204.33, 204.95; HREIMS data: m/z calcd. for $[M+H]^+$ $C_9H_{14}O_2$ 155.2142, obsd 155.2136.

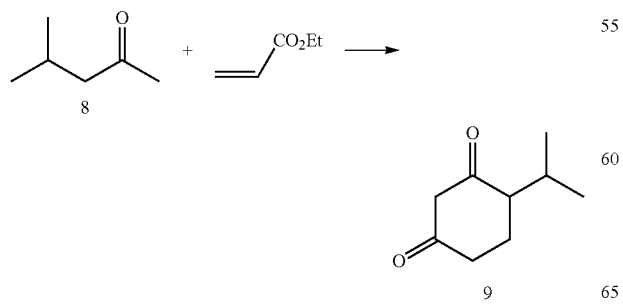

Example 6

Synthesis of Methyl-3-(2,4-dimethoxyphenyl)propanoate (formula 10)

A solution of 3 (100 mg, 0.471 mmol) and iodine (230 mg, 0.94 mmol) in methanol (5 ml) was heated at reflux for 20 h. The reaction mixture was diluted with EtOAc and washed with aq. $NaHSO_3$ and brine solution. The extract was dried over anhydrous $Na_2SO_4$. Purification was done by silica gel chromatography (hexane:EtOAc, 95:5) afforded 10 as yellow gummy liquid (44.19 mg, 41%). $^1$H NMR (300 MHz, $CDCl_3$) δ 2.49 (t, J=7.65 Hz, 2H), 2.79 (t, J=7.75 Hz, 2H), 3.58 (s, 3H), 3.71 (s, 3H), 3.72 (s, 3H), 6.30-6.36 (m, 2H), 6.05 (s, 1H); $^{13}$C NMR (75 MHz, $CDCl_3$) δ 25.67, 34.45, 51.61, 55.37, 55.50, 98.67, 103.98, 121.41, 127.25, 128.72, 130.29, 158.52, 159.73, 174.07; HREIMS data: m/z calcd for $[M+H]^+$ $C_{12}H_{15}O_4$ obsd. 225.2610.

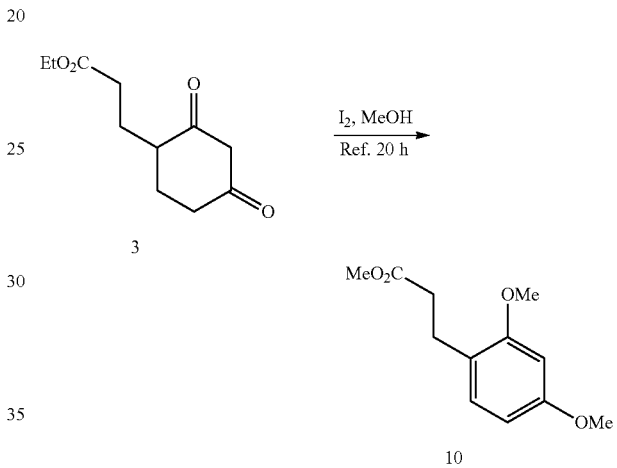

Advantages of the Invention

A simple protocol for the preparation of 3-(2,4-cyclohexanone)-propyl carboxylic acid ethyl ester (CHPC) (3) as a novel product with one chiral center at C-4 using one pot multi component reaction.

A simple process for the preparation of CHPC (3) in gram scale with high yield.

A simple process for the synthesis of cyclohexane-1,3-dione derivatives of unsubstituted and substituted acetone.

A simple process for the preparation of aromatic anisole derivative of propyl ester a very useful intermediate for the synthesis of several natural products.

We claim:

1. A compound of general formula I

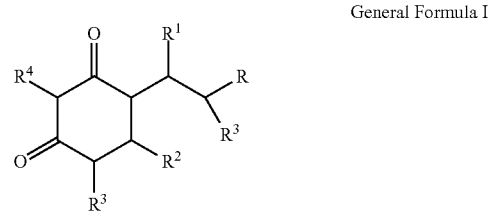

General Formula I wherein R is selected from the group consisting of CO$_2$Y, B(OY)$_2$, CHO, CH(CO$_2$Y)$_2$, PO(OY)$_2$ and CONHZ, wherein Y is selected from the group consisting of hydrogen, alkyl, alkenyl, alkynyl, aryl, heteroaryl, substituted alkyl, substituted alkenyl, cycloalkyl, substituted heteroaryl and tetrazolyl and Z is selected from the group consisting of hydrogen, hydroxyl, alkyl, alkyl-sulfonyl, unsubstituted or substituted aryl sulfonyl, cyanoalkyl and COXM wherein X is S, SO or SO$_2$ and M is selected from the group consisting of hydrogen, alkyl, unsubstituted or substituted alkyl, unsubstituted or substituted aryl, and unsubstituted or substituted heteroaryl;

R$^1$ is selected from the group consisting of hydrogen, alkyl, unsubstituted heteroaryl, substituted heteroaryl, substituted alkyl, and unsubstituted cycloalkyls or substituted cycloalkyls;

R$^2$ is selected from the group consisting of hydrogen, alkyl, unsubstituted aryl, substituted aryl, unsubstituted heteroaryl, substituted heteroaryl, substituted alkyl, and unsubstituted cycloalkyls or substituted cycloalkyls;

R$^3$ is selected from the group consisting of hydrogen, alkyl, alkoxy, and substituted or unsubstituted heteroaryl; and R$^4$ is selected from the group consisting of hydrogen, heteroalkyl, substituted or unsubstituted aryl, unsubstituted or substituted heteroaryl, alkoxy, substituted or unsubstituted aryl carbonyl and substituted keto compounds.

2. A compound selected from the group consisting of:

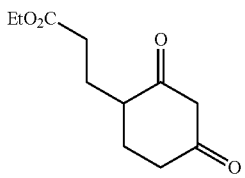

3-(2,4-cyclohexanone)-propyl carboxylic acid ethyl ester

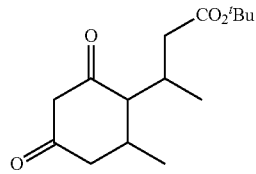 [SMILES: CC1CC(=O)CC(=O)C1C(C)CC(=O)OC(C)(C)C]

and Tert-butyl 3-(2-methyl-4,6-dioxocyclohexyl)butanoate.

3. A single pot process for preparation of compound of general formula I as claimed in claim 1 comprising the steps of:

i. mixing ketone compound of general formula A wherein R is selected from the group consisting of hydrogen and (CH$_2$)$_n$X wherein n is a natural number being 1, 2, 3, 4, 5, 6 or 7 and X comprises hydrogen, unsubstituted or substituted alkyl

General formula A with sodium hydride (NaH) base optionally in presence of a solvent or neat at a temperature in the range of −10° C. to 0° C. to obtain a mixture;

ii. adding α,β-unsaturated ester compound of general formula B wherein R is selected from the group consisting of H, and (CH$_2$)$_n$X wherein n is a natural number being 1, 2 or 3 and X comprises hydrogen, unsubstituted or substituted alkyl, unsubstituted or substituted aryl, R$^1$ is selected from the group consisting of unsubstituted or substituted alkyl group and R$^2$ is selected from the group consisting of hydrogen, unsubstituted or substituted alkyl, unsubstituted or substituted aryl

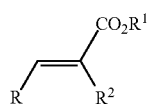

General formula B in to the mixture as obtained in step (i) at a temperature in the range of −10° C. to 0° C. and allowed to attain a temperature of 20-30° C. for a period ranging between 5 minutes to 2 h to obtain mixture;

iii. acidifying the reaction mixture as obtained in step (ii) with HCl maintaining pH in the range of 0 to 3 followed by extracting with ethyl acetate, dichloromethane or chloroform;

iv. removing the solvent from the acidified mixture as obtained in step (iii) to obtain concentrate compound;

v. purifying the concentrate compound as obtained in step (iv) by silica gel column chromatography (hexane:ethylacetate, 7:3) or by solvent extraction to obtain compound of general formula I.

4. The process as claimed in claim 3, wherein said process is useful for the preparation of compound of general formula II wherein R$^6$ is selected from the group consisting of hydrogen, alkyl, alkoxy, unsubstituted or substituted aryl, and unsubstituted or substituted heteroaryl.

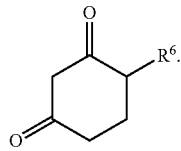

General formula II

5. The process as claimed in claim 4, wherein representative compounds of general formula II comprising:

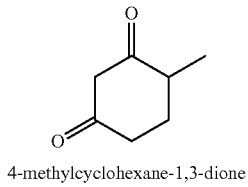

Compound 7

4-methylcyclohexane-1,3-dione

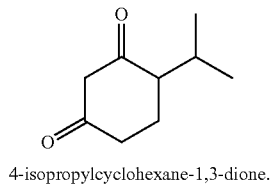

Compound 9

4-isopropylcyclohexane-1,3-dione.

6. The process as claimed in step (i) of claim 3, wherein solvent used is selected from the group consisting of toluene, tetrahydrofuran and benzene.

7. The process as claimed in step (i) of claim 3, wherein molar concentration of sodium hydride (NaH) base is 1.5 to 2 times the number of moles of the ketone.

8. The process as claimed in step (ii) of claim 3, wherein molar concentration of α,β-unsaturated ester is 1 to 2 times the number of moles of the ketone or substituted ketone.

9. The process as claimed in step (v) of claim 3, wherein solvent used for solvent extraction is selected from the group consisting of hexane, ethyl acetate, dichloromethane and chloroform.

10. The compound as claimed in claim 1, wherein said compounds are useful as an intermediate for the synthesis of several biological active heterocycles, natural product analogues, anisoles and aromatic poly phenol derivatives.

11. A process for the preparation of compound of general formula III wherein $R^7$ and $R^8$ are selected from the group consisting of hydrogen, alkyl, unsubstituted or substituted alkyl and whole group $OR^7$ and $OR^8$ are selected from the group consisting of hydrogen, alkyl, substituted or unsubstituted alkyl, unsubstituted or substituted aryl using compound of general formula I as claimed in claim 1,

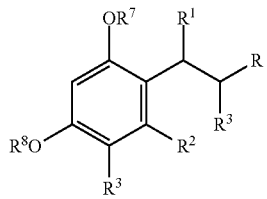

General formula III and the said process comprising the steps of:
(i) reacting compound of general formula I with iodine in methanol or ethanol under reflux for a period ranging between 10 to 20 hr,
(ii) diluting the reaction mixture with ethyl acetate or dichloromethane and washed with $NaHSO_3$ and brine solution, purifying the desired compound by silica gel chromatography (hexane:EtOAc, 95:5)
to obtain compound of general formula III.

12. The process as claimed in claim 11, wherein representative compound of general formula III is

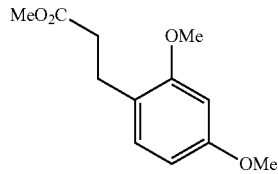

Methyl-3-(2,4-dimethoxyphenyl)propanoate.

* * * * *